US006903223B1

(12) United States Patent
Hatanaka (10) Patent No.: US 6,903,223 B1
(45) Date of Patent: Jun. 7, 2005

(54) PHENYLDIAZIRINE COMPOUNDS AND PHOTOAFFINITY LABELING REAGENT

(75) Inventor: Yasumaru Hatanaka, Toyama (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 09/519,880

(22) Filed: Mar. 6, 2000

(30) Foreign Application Priority Data

Mar. 4, 1999 (JP) .......................................... 11-057255

(51) Int. Cl.⁷ .................... C07D 229/02; C07D 403/12; C07D 495/04; G01N 33/53
(52) U.S. Cl. ........................ 548/960; 548/954; 548/959
(58) Field of Search ................................ 548/954, 959, 548/960; 534/588

(56) References Cited

PUBLICATIONS

Yasumaru Hatanaka, et al., "Diazirine–Based Photoaffinity Labeling: Chemical Approach to Biological Interfaces", Reviews on Heteroatom Chemistry, vol. 14, pp. 213–243 (1996).
Yasumaru Hatanaka, "Organic Chemistry for Structural Biology: Probing the Functional Structure of Proteins by Photoaffinity Labeling", vol. 56, No. 7, pp. 581–590 (1998).
Makoto Hashimoto, et al., "Identification of Photolabeled Peptides for the acceptor Substrate Binding Domain of β1, 4–Galactosyltransferase", Chem. Pharm. Bull., vol. 47(5), pp. 667–671 (May 1999).
Yasumaru Hatanaka, et al. "A Novel Biotinylated Heterobifunctional Cross–Linking Reagent Bearing an Aromatic Diazirine", Bioorganic & Medicinal Chemistry, vol. 2, No. 12, pp. 1367–1373 (1994).
Françoise Koumanov, et al., "Cell–Surface Biotinylation of Glut4 Using Bis–Mannose Photolables", Biochem J., vol. 330, pp. 1209–1215 (1998).
Yasumaru Hatanaka, et al., "A Rapid and Efficient Method for Identifying Photoaffinity Biotinylated Sites Within Proteins", J. Am. Chem. Soc., vol. 120, pp. 453–454 (1998).

Yasumaru Hatanaka, et al., "Synthesis and Characterization of a Carbene–Generating Biotinylated N–Acetylglucosamine for Photoaffinity Labeling of β–(1→4)–Galactosyltransferase", Carbohydrate Research, vol. 294, pp. 95–108 (1996).
Yasumaru Hatanaka, Pharmacia, vol. 34, No. 8 pp. 772–776 (1998).

*Primary Examiner*—James O. Wilson
*Assistant Examiner*—Howard V Owens
(74) *Attorney, Agent, or Firm*—Oblon, Spivak, McClelland, Maier & Neustadt, P.C.

(57) ABSTRACT

This invention offers a photoreactive labeling reagent consisting of a novel biotinylated phenyldiazirine compound; a photoaffinity labeling reagent consisting of a saccharide-linked biotinylated phenyldiazirine compound where a saccharide compound is introduced into the novel compound; and a novel diazirine compound for such a reagent. The invention covers a biotinylated phenyldiazirine compound of the following formula (II); a phenyldiazirine compound which is an intermediate for synthesizing the above; a saccharide-linked biotinylated phenyldiazirine compound derived from the compound of the formula (II) and a saccharide compound and a method for manufacturing the same; a photoreactive labeling reagent containing the compound of the formula (II); a photoaffinity labeling reagent containing the saccharide-linked biotinylated phenyldiazirine compound; and a method for labeling a saccharide receptor using the reagent.

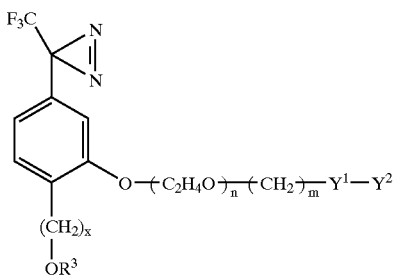

(II)

19 Claims, 6 Drawing Sheets

PHENYLDIAZIRINE COMPOUNDS AND PHOTOAFFINITY LABELING REAGENT

BACKGROUND OF THE INVENTION

1. Field of the Invention

The present invention relates to novel phenyldiazirine compounds, biotinylated phenyldiazirine compounds and saccharide-linked biotinylated phenyldiazirine compounds. It further relates to a photoreactive labeling reagent consisting of the biotinylated phenyldiazirine compound expected to be used as a probe for analysis of structure of biosubstances and also to a photoaffinity labeling reagent consisting of the saccharide-linked biotinylated phenyldiazirine compound.

2. Description of the Related Art

Photoaffinity labeling reagents have been known as useful probes which are able to analyze the interacting moiety of pharmaceuticals or ligand with protein. An azide group has been known already as a photoreactive group for labeling the protein by means of a photoreaction and, as a better photoreactive group, a diazirine group has been receiving attention. Introduction of a diazirine group into a ligand derived from biosubstances and pharmaceuticals is usually carried out by means of an amide bond or an ester bond and, for further object of a microdetection, it is converted to a radioactive derivative.

Quite recently, phenyldiazirine derivatives having a biotin residue via a spacer compound in a molecule have been developed as the substances which are able to achieve both affinity purification and microdetection of protein and, for example, it has been reported that non-radioactive photoaffinity labeling reagent can be synthesized by linking a saccharide compound as a ligand derived from biosubstances with a carboxyl group of the diazirine derivative (cf. Yuki Gosei Kagaku Kyokaishi, Vol. 56, No. 7, pages 581–590 (1998); Pharmacia, Vol. 34, No. 8, pages 772–776 (1998); Biochem. J., 330, 1209–1215 (1998); J. Am, Chem. Soc. Vol. 120, pages 453–454 (1998); Bioorganic & Medicinal Chemistry, Vol. 2, No. 12, pages 1367–1373 (1994); Carbohydrate Research, Vol. 294, pages 95–108 (1996); Reviews on Heteroatom Chem., Vol. 14, pages 213–243 (1996); and Chem. Pharm. Bull., Vol. 47, pages 667–671 (1999)). However, according to such a method, it is necessary in linking a saccharide compound to the diazirine compound that an amino group is previously introduced into the saccharide compound and that a carboxyl group of the diazirine compound is made to react therewith in the presence of a condensing agent such as dicyclohexylcarbodiimide (DCC) and, therefore, the operation is troublesome.

On the other hand, as a method for a specific modification of a biosubstance, utilization of an oxyamino group has been receiving attention although an attempt of introducing the oxyamino group into a photoreactive compound and to link to a saccharide compound has not been carried out yet.

SUMMARY OF THE INVENTION

An object of the present invention is to offer a photoreactive labeling reagent containing a novel biotinylated phenyldiazirine compound which can be converted to a photoreactive probe having no necessity of radioactive labeling and also to offer a photoaffinity labeling reagent containing a non-radioactive saccharide-linked biotinylated phenyldiazirine compound which is expected to be useful for the investigation of function and structure of biopolymers such as protein (saccharide receptor) which is able to interact with a saccharide. Further object of the present invention is to offer novel biotinylated phenyldiazirine compound useful for constituting those labeling reagents, saccharide-linked biotinylated phenyldiazirine compound and those compounds wherein a biotin residue is bound to a phenyldiazirine compound via a cleavable spacer if desired, a novel phenyldiazirine compound which is an intermediate for the synthesis of those compounds, a method for the manufacture of the novel saccharide-linked biotinylated phenyldiazirine compound, and a method for labeling the saccharide receptor by the compound.

The essential feature of the present invention is a biotinylated phenyldiazirine compound represented by at least one of the formulae (I) to (IV), a phenyldiazirine compound represented by the formula (I) which is an intermediate for the synthesis of the above (I) to (IV), and a saccharide-linked biotinylated phenyldiazirine compound represented by at least one of the formulae (V) to (VII) which is derived from at least one of the compounds represented by the formulae (II) to (IV) respectively while another essential feature of the present invention is a photoreactive labeling reagent containing at least one of the compounds represented by the formulae (II) to (VI) and a photoaffinity labeling reagent consisting of a saccharide-linked biotinylated phenyldiazirine compound represented by at least one of the formulae (V) to (VII). Another essential feature of the present invention is a method for the manufacture of the saccharide-linked biotinylated phenyldiazirine compound represented by at least one of the formulae (V) to (VII) by the reaction of a biotinylated phenyldiazirine compound represented by at least one of the formulae (II) to (IV) with a saccharide compound having a reducing end and a method for labeling the saccharide receptor using the saccharide-linked biotinylated phenyldiazirine compound.

DETAILED DESCRIPTION OF THE INVENTION

An intermediate compound for producing a compound which constitutes a photoaffinity labeling reagent in the present invention may be, in essence, a phenyldiazirine derivative in which trifluoromethylphenyldiazirine having a diazirine group as a photoreactive group whereby a saccharide receptor protein is labeled by a photoreaction is a fundamental skeleton and a group having a labeling compound and a group having an amino group to which a ligand such as saccharide can be bound are bonded to the benzene nucleus. To be more specific, in the phenyldiazirine derivative, a group selected from an amino group, salt of an amino group, a protected amino group, etc. is bound to the benzene nucleus via a spacer such as an alkylene group and, in order to reduce the influence on a binding ability of the ligand by a photoreactive group of a diazirine type, it is bound at a para-position to the bound position of the photoreactive group. Further, in a group having a labeling compound, a labeling compound such as biotin is bound to the benzene nucleus via a hydrophilic spacer containing a polyoxyethylene group and the like. In this case, biotin which is a labeling compound can be bound to the benzene nucleus via a terminal amino group of the spacer. On the other hand, when a biotinylated saccharide-receptor (labeled protein) is isolated and recovered by means of an affinity purification using an avidin-imobilized carrier (immobilized avidin), there is a case that the binding of biotin and immobilized avidin usually used for the separation and purification is too strong and the recovery rate of the labeled protein is sometimes lowered and therefore, it is preferable to bind them via a spacer having a cleavable property so as to separate the labeled protein from biotin under a mild condition. For example, biotin can be bound to the benzene nucleus via a spacer wherein a cleavable spacer such as acylsulfonamide is introduced into the end of polyoxyethylene group.

The photoreactive biotinylated phenyldiazirine compound of the formula (II) of the present invention is a representative example of such a derivative.

The compound of the present invention represented by the following formula (I) is an intermediate for the synthesis of a biotinylated phenyldiazirine compound represented by the formula (II) and is a novel compound.

(I)

In the formula (I), $R^1$ is —$NHP^1$ or —$COX^1$; $R^2$ is an aldehyde group, a hydroxy lower alkyl group, a halogenated lower alkyl group, a phthalimidoxy lower alkyl group or —$(CH_2)_x$—O—$NHP^1$; $P^1$ is a protecting group for an amino group; $X^1$ is an alkoxy group, hydroxyl group or —$NHSO_2$—$X^2$—CO—$X^3$; $X^2$ is an arylene group or an alkylene group; $X^3$ is an alkoxy group or hydroxyl group; m is an integer of 1–4 or, preferably, 1–2; and n is an integer of 1–6 or, preferably, 1–4; x is an integer of 1 to 4 or, preferably, 1 to 2.

In the present invention, a lower alkyl group means an alkyl group having 1–4 carbon(s) such as methyl, ethyl, propyl and butyl and a linear group is preferred. An alkoxy group means an alkoxy group hanving 1–6 carbon(s) such as methoxy, ethoxy, propoxy, butoxy and pentoxy. An arylene group means an arylene group having 5–14 carbon(s) such as phenylene group or naphthylene group which may have a substituent such as methyl or ethyl and phenylene group is preferred. An alkylene group is an alkylene group having 1–6 carbon(s) such as methylene, ethylene, propylene, or butylene and a linear group is preferred.

Examples of a protective group for an amino group are a tert-butoxycarbonyl group, a trifluoroacetyl group, a benzyloxycarbonyl group, a p-methoxybenzyloxycarbonyl group, a p-toluenesulfonyl group, a 9-fluorenylmethyloxycarbonyl group, a trityl group, a phthaloyl group, an O-nitrophenylsulfenyl group and a 3-nitro-2-pyridinesulfenyl group. Among them, a tert-butoxycarbonyl group is convenient.

The biotinylated phenyldiazirine compound of the present invention is a compound represented by the following formula (II) and is prepared in such a manner that the compound of the above formula (I) is biotinylated and, if desired, $R^2$ is converted to an aminoxy lower alkyl group.

(II)

In the formula (II), $R^3$ is a phthalimide group, an amino group, —$NHP^1$ or salt of an amino group; $P^1$ is a protecting group for an amino group; m is an integer of 1–4 or, preferably, 1–2; n is an integer of 1–6 or, preferably, 1–4; and x is an integer of 1–4 or, preferably, 1–2. The protecting group for an amino group is the same as that mentioned in the above formula (I). Examples of salt of an amino group are a salt with an inorganic acid such as hydrochloric acid, sulfuric acid, nitric acid and phosphoric acid and that with an organic acid such as acetic acid, trifluoroacetic acid, propionic acid and methanesulfonic acid. Among them, trifluoroacetic acid is advantageous for the production of the compound of the formula (V).

$Y^1$ is —NH— or —$CONHSO_2$—$X^2$—CO—; $X^2$ is an arylene group or an alkylene group; and $Y^2$ is a biotin residue or a biotin derivative residue. And an arylene group and an alkylene group are the same as those mentioned in the above formula (I).

A biotin derivative of this invention means a biotin derivative wherein the terminal group (—OH) of biotin is substituted with a group capable of reacting with an amino group or a carboxyl group and a compound represented by biotin-NH—$Z_q$—$NH_2$ having an amino group at the terminus, preferably biotin hydrazide, is exemplified as a biotin derivative having a group capable of reacting with a carboxyl group.

More concretely, a compound represented by the formula (III) or (IV) is exemplified as a compound of the formula (II).

(III)

In the formula (III), $R^3$, $P^1$, m, n and x are the same as those mentioned in the formula (II).

(IV)

In the formula (IV), $R^3$, $P^1$, m, n and x are the same as those mentioned in the formula (II); $X^2$ is an arylene group or an alkylene group and is the same as that in the formula (I); Z is an alkylene group having 1 to 20 carbon atoms which may be interrupted by a hetero atom such as oxygen, sulfur and nitrogen, for example, methylene, ethylene, propylene or (poly)oxyethylene group; and q is 0 or 1.

The saccharide-linked biotinylated phenyldiazirine compound represented by the following formulae (V) to (VII) is a compound which is prepared by the reaction of a biotinylated phenyldiazirine compound of the formulae (II) to (VI) having a terminal amino group or amino group salt with an aldehyde group of a reducing end of a saccharide compound having a reducing end.

In the formula (V), $R^4$ is a residual group of a saccharide compound having a reducing end; m is an integer of 1–4 or, preferably, 1–2; n is an integer of 1–6 or, preferably, 1–4; x is an integer of 1–4 or, preferably, 1–2; $Y^1$ is —NH— or —$CONHSO_2$—$X^2$—CO—; $X^2$ is an arylene group or an alkylene group; and $Y^2$ is a biotin residue or a biotin derivative residue and is the same as that mentioned in the formula (II).

A compound represented by the formula (VI) or (VII) of this invention is more definite compound of the compound of formula (V).

(VI)

In the formula (VI), $R^4$, m, n and x are the same as those mentioned in the formula (V).

(VII)

In the formula (VII), $R^4$, m, n, x, and $X^2$ are the same as those mentioned in the formula (V); and Z and q are the same as those mentioned in the formula (IV). The compound represented by the formula (VII) is a saccharide-linked biotinylated phenyldiazirine compound having a cleavable spacer and especially, the compound wherein $X^2$ is a phenylene group and q is 0 is preferable as a compound constituting the photoaffinity labeling reagent useful for isolation and recovery of the biotinylated protein.

Examples of the saccharide compound to be reacted with the compounds of formulae (II) to (IV) are reducing end-having polysaccharide, oligosaccharide and monosaccharide such as mucin-type saccharide, Asn-type saccharide, sialylsaccharide, glycosaminoglycan, lactosamine, N-acetyllactosamine, lactosamine oligosaccharide, sialyllactosamine, glucan, mannan, fructan, galactan, polyuronic acid, oligoaminosaccharide, polyaminosaccharide and galacto-oligosaccharide. More specific examples of $R^4$ are an N-acetyllactosyl group, a sialyl-α2-3-lactosyl group, a sialyl-α2-3-N-acetyllactosaminyl group, a Lewis X-type trisaccharide residue, a sialyl Lewis X-type tetrasaccharide residue and chitobiose residue, although $R^4$ is not limited thereto so far as it is a saccharide compound which is able to bind as shown in the following scheme. Thus, a bond of a compound of the formula (II) of the present invention where $R^3$ is an amino group or an amino group salt with a saccharide compound having a reducing end is selective and the bond is shown as follows.

[Saccharide Compound Residue-CHO + NH$_2$O-[Diazirine Compound] or
$^+$NH$_3$O-[Diazirine Compound]

-continued
[Saccharide Compound Residue]-CH═N—O-[Diazirine Compound]

⇅

The reaction of the compound of the present invention represented by the formulae (II) to (IV) where $R^3$ is an amino group or an amino group salt with a saccharide compound having a reducing end is dependent upon pH and the reaction advantageously proceeds under a weakly acidic condition. Usually, the reaction proceeds at pH 1–7 and, preferably, the reaction is carried out after adjusting the pH to 4–5 using a buffer.

One kind of the photoreactive biotinylated phenyldiazirine compound of the present invention represented by the formulae (II) to (IV) has a characteristic feature that an oxyamino group (aminoxy group) is introduced into its phenyl skeleton via a spacer and the oxyamino group binds to an aldehyde group at a reducing end of a reducing end-having saccharide compound by means of a reaction forming a Schiff's base without requiring a protection of the hydroxyl group on the saccharide chain and in the absence of a condensing agent which has been necessary to date such as DCC but by a mere mixing with the saccharide compound whereupon a saccharide-linked biotinylated phenyldiazirine compound represented by the formulae (V) to (VII) is produced. The photoaffinity labeling reagent of the present invention can be constituted essentially by that compound and may contain additives such as water, buffer, stabilizer, salt or the like unless the function of that compound is lessened. Besides, the oxyamino group of the formulae (II)

to (IV) can be bound to a ketone group or a carboxyl group other than an aldehyde group and therefore, in case that the sacccharide compound has such the functional group, the oxyamino group may be reacted with such the functional group. Incidentally, a photoaffinity labeling reagent means, in a broad sense, a labeling reagent where a ligand links to a compound having a photoreactive group but, in the present specification, the term "photoaffinity labeling reagent" stands for a photoreactive labeling reagent having an affinity to a saccharide receptor where the saccharide receptor stands for protein having an affinity to a saccharide or, in other words, that having a binding property to a saccharide due to a specific interaction with the saccharide. To be more specific, it covers saccharide-specific lectin, receptor, enzyme, antibody, etc.

In a mixed system containing the photoaffinity labeling reagent of the present invention and various kinds of protein, when light is irradiated together with or after the interaction of a saccharide compound of the labeling reagent with a saccharide receptor, a diazirine group of the labeling reagent cross-links by means of a photoreaction to the interacting moiety (amino acid) to the saccharide compound, of the protein (saccharide receptor) which specifically interacts with a saccharide compound of the photoaffinity labeling reagent. Further, the protein which is labeled with the photoaffinity labeling reagent containing biotin can be detected in a high sensitivity by means of a detecting system which has been known for the detection of biotin and, when an avidin column where avidin, streptoavidin, or the like is bound to a carrier is utilized, an aimed protein can be easily purified by means of an affinity chromatography. Furthermore, in this invention, when a compound wherein biotin is bound via a cleavable spacer is applied as a saccharide compound constituting the photoaffinity labeling reagent, the biotin moiety can be separated easily under a mild condition during or after the affinity chromatography using avidin column and the aimed protein can be recovered at high yield. Accordingly, the photoaffinity labeling reagent of the present invention linked to a saccharide compound is expected to be a very useful probe or purifying means in the analysis of structure and function of protein which is related to saccharide chain.

An oxyamino group of the biotinylated phenyldiazirine compound of the present invention represented by the formula (II) having an oxyamino group on a phenyl skeleton may be, if necessary, linked to a component excepting a saccharide compound, such as a pharmaceutical or a component derived from living matter into which a functional group capable of reacting with the oxyamino group, such as an aldehyde group, a ketone group or an carboxyl group is introduced whereby a photoaffinity labeling reagent in a broad sense can be obtained. It is possible to use this labeled reagent for the analysis of structure and function or isolation and purification of protein having affinity to the substance derived from living matter other than a saccharide compound or a pharmaceutical and, therefore, the compound of the present invention represented by the formula (II) is a compound having a broad usefulness.

The method may be applicable to any other ligands bearing functional groups, such as ketone, aldehyde, or carboxyl, that can be connected to the oxyamino moiety. Furthermore, a combination of the present method with the combinatorial technology and mass spectrometry may extend the potential of photoaffinity labeling to a rapid and sensitive way for elucidating the protein structure.

An example of the synthesis of the compounds of the present invention will be illustrated below by referring to the reaction scheme as shown in FIG. 1 to FIG. 6.

Figure 1:
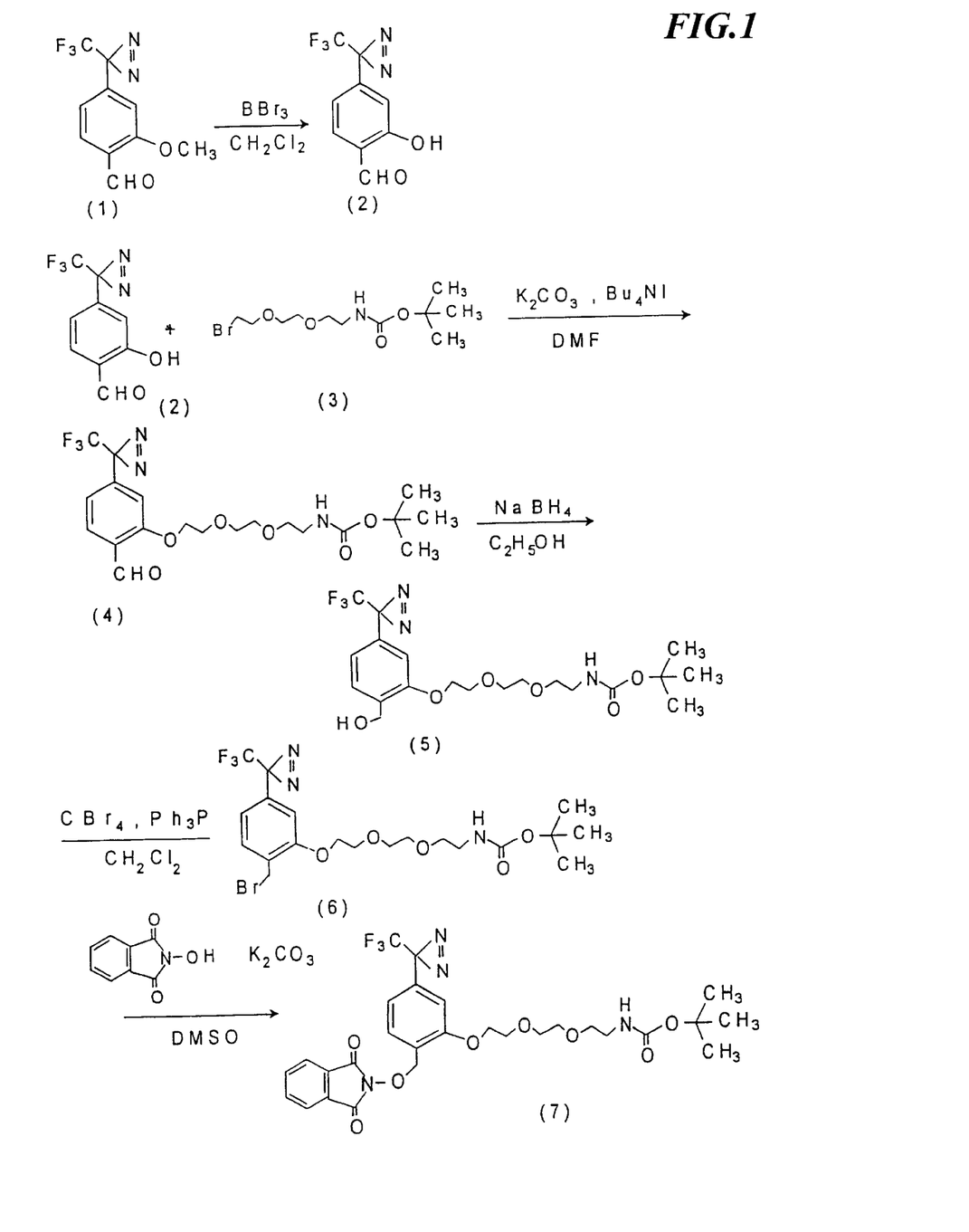
FIG. 1 is an outline of the reaction scheme showing an example for the synthesis of the compound of the formula (I) of the present invention.

First, in accordance with the reaction steps as shown in FIG. 1, the manufacturing steps for the compounds of the present invention represented by the formula (I), i.e. the compounds (4)–(7) in FIG. 1, will be illustrated.

The compound (1) [2-methoxy-4-(1-azi-2,2,2-trifluoroethyl)benzaldehyde] which is a starting material may be prepared by a method of Hashimoto, et al. (M. Hashimoto, Y. Kanaoka, Y. Hatanaka: Heterocycles, vol. 46, pages 119–122 (1997)).

When the compound (1) is treated with boron tribromide ($BBr_3$) at around −20° C. in an inert gas atmosphere in a solvent such as dichloromethane, the compound (2) is produced.

When the resulting compound (2) is made to react with the compound (3) in the presence of a base such as anhydrous potassium carbonate and a phase transfer catalyst such as tetrabutylammonium iodide ($Bu_4NI$), the compound (4) is produced. This reaction may be carried out in dimethylformamide (DMF) in an atmosphere of inert gas at around 60° C. Incidentally, the compound (3) is a compound of the formula $P^1NH(CH_2)_m(OC_2H_4)_n$—Br where m=n=2 and $P^1$ is a tert-butoxycarbonyl group and can be prepared by a method of Hatanaka, et al. (Y. Hatanaka, M. Hashimoto, Y. Kanaoka; Bioorg. Med. Chem., vol. 2, pages 1367–1373 (1994)).

When the compound (4) is reduced at about room temperature using sodium borohydride ($NaBH_4$) in a solvent such as ethanol, the compound (5) is prepared. The product of this reducing reaction may be used in the following reaction step without further purification.

The resulting compound (5) is brominated with carbon tetrabromide and triphenylphosphine in a solvent such as dichloromethane to give the compound (6). This reaction is preferably carried out by cooling at around 0° C.

When the compound (6) is made to react with N-hydroxyphthalimide in the presence of a base such as anhydrous potassium carbonate, the compound (7) is prepared. This reaction may be carried out at around room temperature in a solvent such as dimethyl sulfoxide (DMSO).

Figure 2:
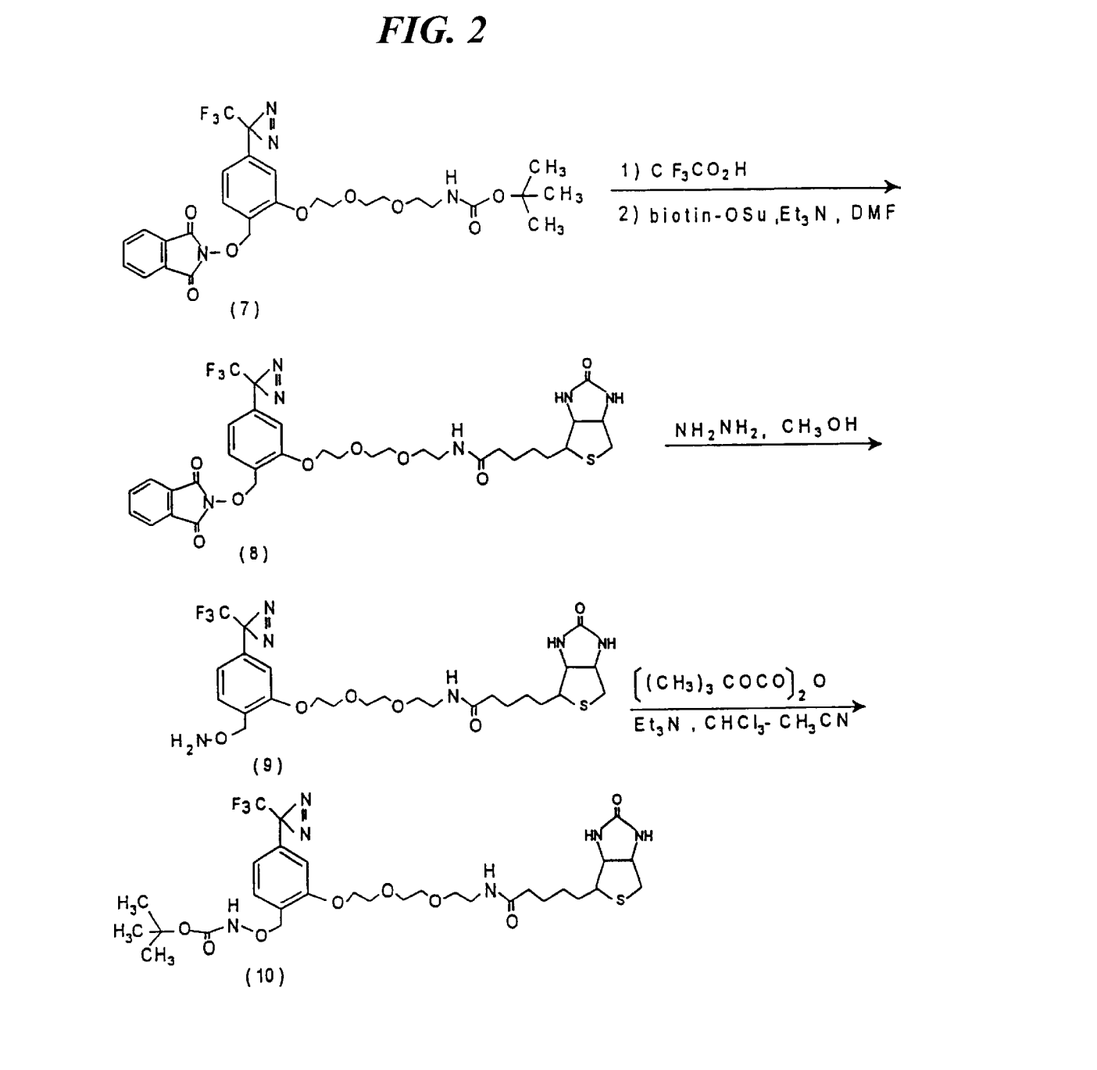
FIG. 2 is an outline of the reaction scheme showing an example for the synthesis of the compound of the formula (II) of the present invention.

Next, in accordance with FIG. 2, the manufacturing steps for the compounds of the present invention represented by the formula (II), especially the compounds of the formula (III), i.e. the compounds (8)–(10) in FIG. 2, after biotinylation of the compound (7) will be illustrated.

After the compound (7) is treated with trifluoroacetic acid at around 0° C. in an organic solvent such as dichloromethane, it is made to react with N-hydroxysuccinimide ester of biotin (biotin-Osu) in a solvent such as DMF in the presence of an organic base such as triethylamine ($Et_3N$) whereupon the biotinylated compound (8) is prepared.

When the compound (8) is treated with anhydrous hydrazine at around room temperature in a solvent such as methanol, the compound (9) can be produced but, since this compound (9) is apt to be decomposed during purification by a column chromatography, it is preferred to use in the next reaction without further purification.

The compound (9) which is a reaction product of the compound (8) with hydrazine is directly made to react with di-t-butyl dicarbonate [$(CH_3)_3COCO]_2O$ in the presence of an organic base such as triethylamine in a mixed solvent consisting of chloroform and acetonitrile for example whereupon the compound (10) can be prepared.

Figure 3:
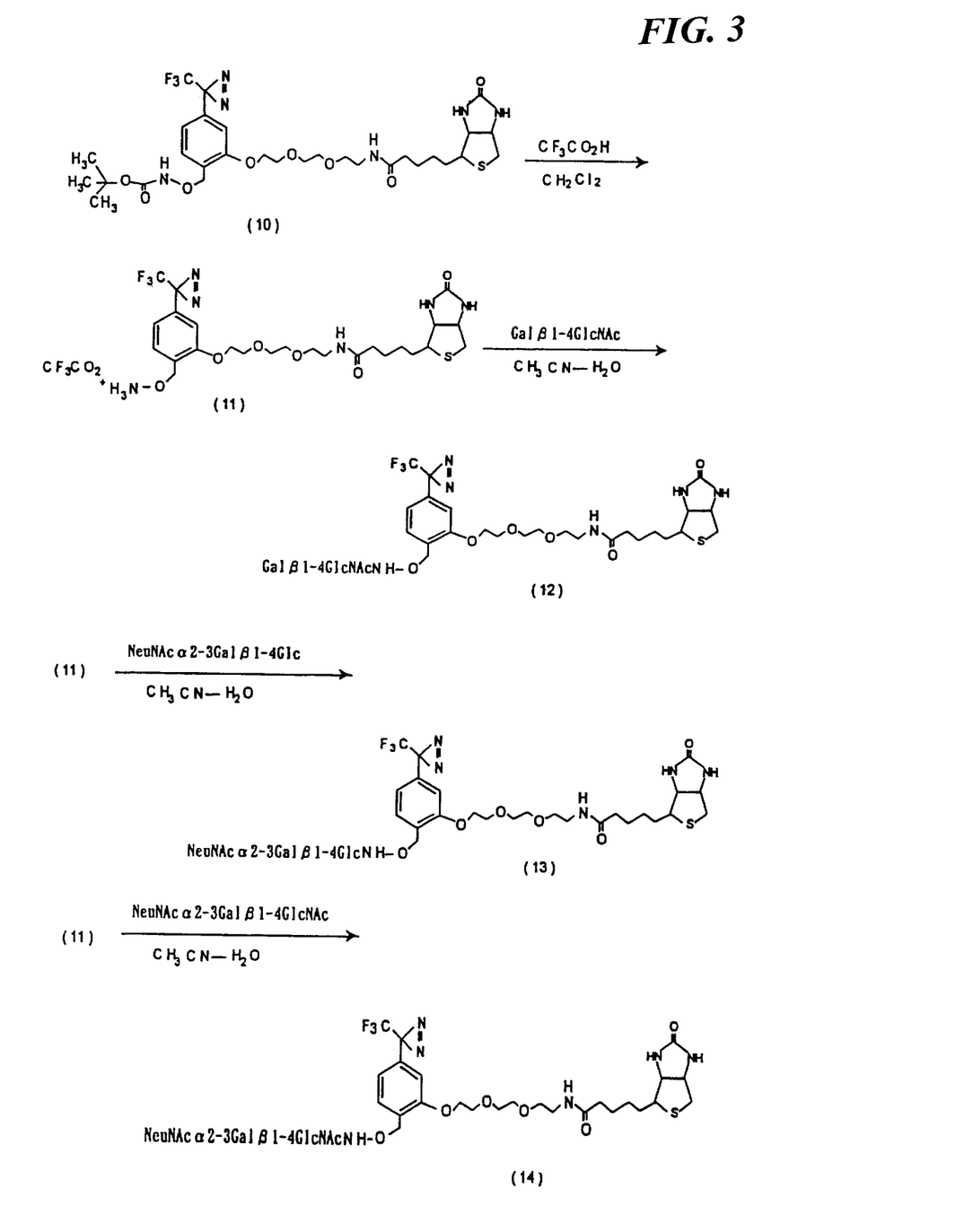
FIG. 3 is an outline of the reaction scheme showing an example for the synthesis of the compound of the formula (V) of the present invention.
Figure 4:
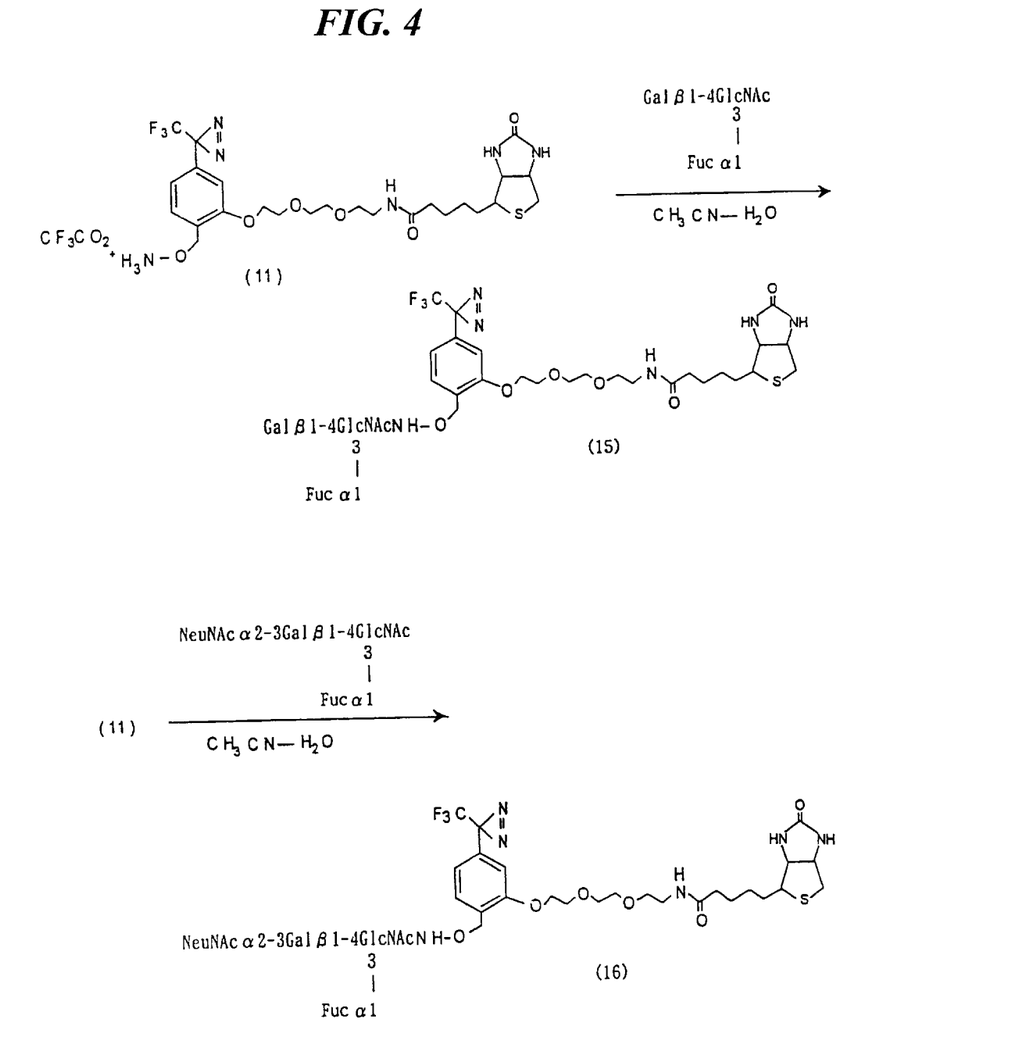
FIG. 4 is an outline of the reaction scheme showing an example for the synthesis of the compound of the formula (V) of the present invention.

Further, as shown in FIG. 3 and FIG. 4, a saccharide compound having a reducing end is introduced into the biotinylated phenyldiazirine compound prepared in the above steps to prepare the compound of the present invention represented by the formula (V), especially the compounds of the formula (VI), i.e. the compounds (12)–(16).

The compound (10) is made to react with trifluoroacetic acid at around 0° C. in an organic solvent such as dichloromethane to give the compound (11). The resulting compound (11) is immediately made to react with various saccharide compounds having a reducing end to give biotinylated phenyldiazirine compounds linked to those saccharide compounds. For example, when the compound (11) is made to react with N-acetyllactosamine (Galβ1-4GlcNAc) in an aqueous acetonitrile at around 37° C. to give the compound (12). Similarly are prepared the compounds (13)–(16) by the reaction with sialyl-α2-3-lactose (NeuNAcα2-3Galβ1-4Glc), sialyl-α2-3-N-acetyllactosamine (NeuNAcα2-3Galβ1-4GlcNAc), Lewis X type trisaccharide (Galβ1-4(Fucα1-3)GlcNAc) and sialyl Lewis X type tetrasaccharide (NeuNAcα2-3Galβ1-4(Fucα1-3)GlcNAc), respectively. It is also possible, instead of using trifluoroacetic acid to be made to react with the compound (10), to prepare salts with inorganic acid by the use of hydrochloric acid/acetic acid, hydrochloric acid/dioxane mixture, etc.

Figure 5:
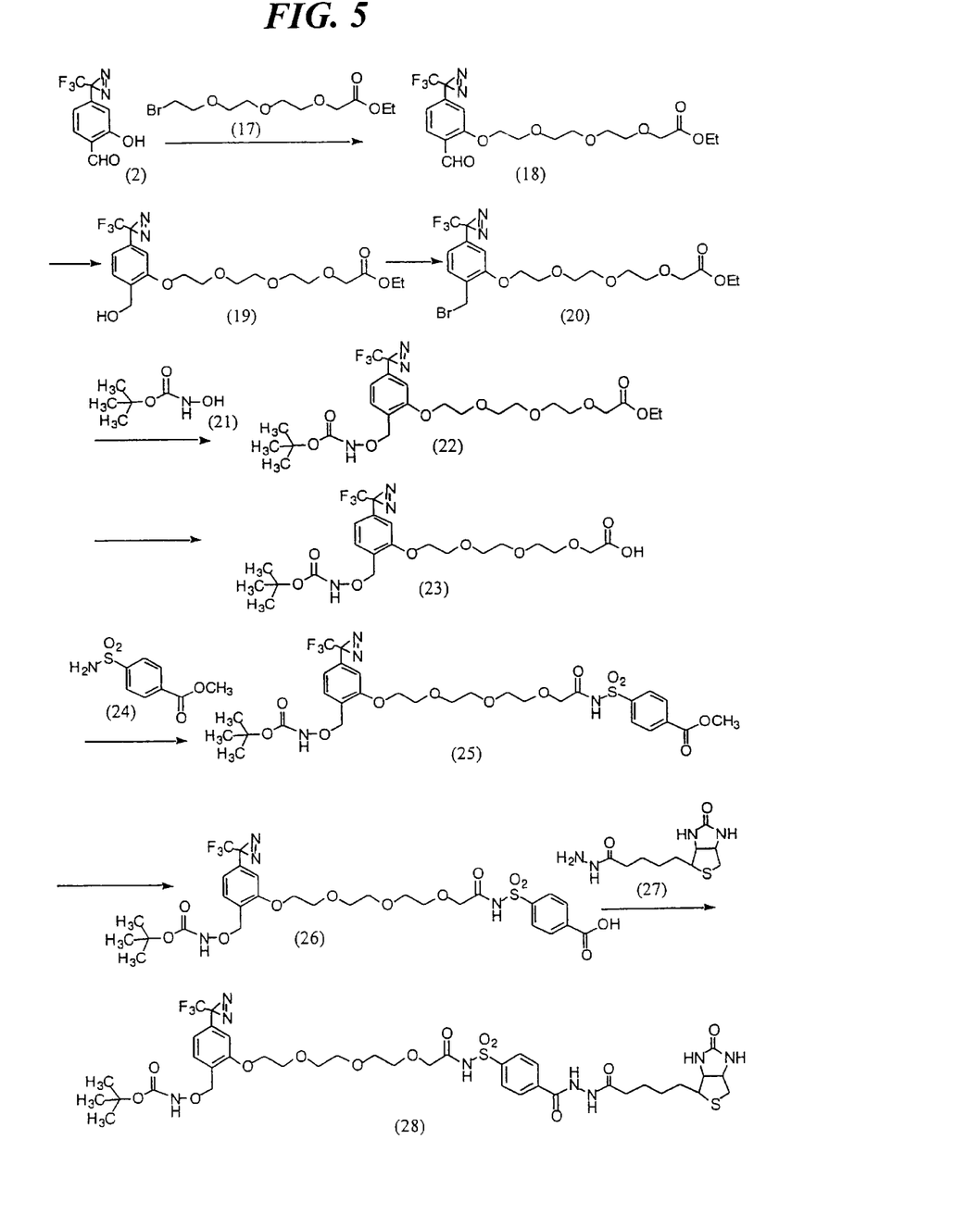
FIG. 5 is an outline of the reaction scheme showing an example for the synthesis of the compounds of the formulae (I) and (IV) of the present invention.
Figure 6:
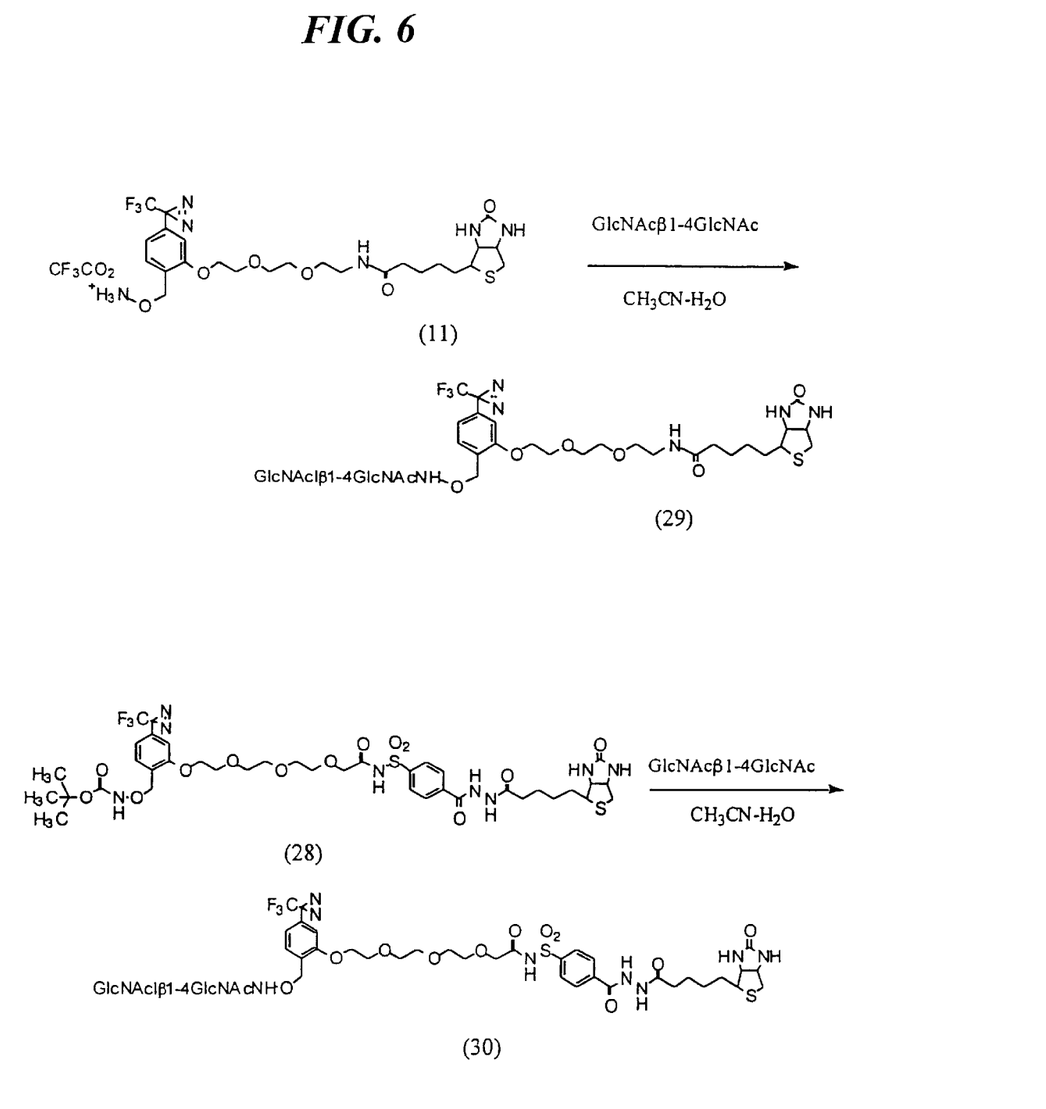
FIG. 6 is an outline of the reaction scheme showing an example for the synthesis of the compounds of the formula (V) of the present invention.

Then, an example of the synthesis of the compounds represented by the formula (I), i.e. the compounds (18)–(20), (22), (23), (25) and (26) in FIG. 5 and FIG. 6, the compounds having a cleavable spacer represented by the formulae (IV) and (VII), i.e. the compounds (28) and (30) in FIG. 5 and FIG. 6 and additionally, the compound (29) of the formula (VI) will be illustrated below by referring to the reaction scheme as shown in FIG. 5 and FIG. 6.

The compound (2) can be synthesized from the compound (1) in accordance with the process as shown in FIG. 1. The compound (2) is made to react with the compound (17) in the presence of a base such as anhydrous pottasium carbonate and a phase transfer catalyst such as $Bu_4NI$ to produce the compound (18). The reaction may be carried out in a solvent such as dimethylsulfoxide (DMSO) in an atmosphere of inert gas at around 60° C. Incidentally, the compound (18) is a compound of the formula (I) where $R^2$ is an aldehyde group, $R^1$ is $—COX^1$, $X^1$ is an ethoxy group, m is 1 and n is 3.

On the other hand, the compound (17) can be synthesized as follows. That is, 2-[2-(2-chloroethoxy)ethoxy]ethanol is made to react with ethyl bromoacetate at −70° C. in toluene solvent containing sodium hydride, the resulting reaction mixture is distilled to remove the solvent and the thus obtained residue is purified by a column chromatography. The purified residue is dissolved in a solvent such as N-methylpyrrolidone and made to react at around 65° C. after adding ethyl bromide and sodium bromide and the reaction product is distilled to remove the solvent and further, purified by a column chromatography.

The compound (18) is reduced by using $NaBH_4$ in a solvent such as ethanol at around room temperature to produce the compound (19). The resulting compound (19) is brominated with carbon tetrabromide and triphenylphosphine in a solvent such as dichloromethane to give the compound (20). This reaction is preferably carried out by cooling at around 0° C.

The compound (20) is made to react with N-hydroxycarbamic alkylester (compound (21)) such as t-butyl N-hydroxycarbamate in the presence of a base such as sodium hydride to produce the compound (22). This reaction may be carried out in a solvent such as tetrahydrofuran (THF) at around 0° C.

The compound (22) is hydrolyzed in a mixed solvent consisting of ethanol and alkali aqueous solution for example to produce the compound (23). The resulting compound (23) and carbonylimidazole are dissolved in a solvent such as THF and is made to react with the compound (24) such as sulfamoylbenzoic ester which is a compound for giving cleavable property to the spacer in the presence of an organic base such as diisopropylethylamine to produce the compound (25).

The compound (24) used for giving cleavable property is selected suitably in consideration of the kind of saccharide compound contained in the labeling reagent of this invention and the kind of protein being a saccharide receptor which specifically interacts with said saccharide compound and as sulfamoylbenzoic ester can be cleaved under a mild condition and is high in stability, it is used preferably.

The compound (25) is hydrolyzed in a mixed solvent consisting of ethanol and alkali aqueous solution for example to produce the compound (26), the resulting compound (26) is made to react with N-hydroxysuccinimide and carbodiimide compound (DCC etc.) and thus obtained activated ester is biotinylated by reacting with a biotin derivative such as the compound (27), biotinhydrazide, to produce the biotinylated phenyldiazirine compound (28) having a cleavable spacer.

To the compound (28), the saccharide compound (chitobiose: GlcNAcβ1-4GlcNAc) is introduced according to the process same as that shown in FIG. 3 and FIG. 4 to produce the saccharide-linked biotinylated phenyldiazirine compound (30) having a cleavable spacer. On the other hand, to the above mentioned compound (11), chitobiose is introduced as a saccharide compound having a reducing end to produce the compound (29) not having a cleavable spacer.

The present invention will now be further illustrated by way of the following examples although the present invention. is not limited thereto unless it deviates from the essential feature thereof. Incidentally, in the example, the compound numbers correspond to those described in FIG. 1 to FIG. 6.

EXAMPLE 1

Manufacture of the Compound (2) from the Compound (1)

Boron tribromide (3.76 g, 15 mmol) was slowly dropped into a solution of the compound (1) (3.66 g, 15 mmol) in dichloromethane (30 ml) at −20° C. in an argon atmosphere. After stirring the mixture at 0° C. for one hour, water was added. The reaction mixture was extracted with dichloromethane and the extract was dried over anhydrous magnesium sulfate. After evaporation of the solvent, the residue was chromatographed on silica gel (eluting with dichloromethane:hexane=1:2) to give 3.18 g (92%) of the compound (2) {2-hydroxy-4-[3-(trifluoromethyl)-3H-diazirine-3-yl]benzaldehyde as a white solid.

IR (Nujol): ν=3170, 1665 $cm^{-1}$; $^1H$ NMR (400 MHz, $CDCl_3$, 25° C.): δ=11.05 (s, 1H), 9.92 (s, 1H), 7.60 (d, J=8.0 Hz, 1H), 6.78 (d, J=8.0 Hz, 1H), 6.77 (br s, 1H); MS ($EI^+$): m/z (%): 230 (38) $[M^+]$; HRMS: calcd. for $C_9H_5F_3N_2O_2$ $[M^+]$=230.0303, found: 230.0291.

EXAMPLE 2

Manufacture of the Compound (4) from the Compounds (2) and (3)

A mixture of the compound (2) (2.76 g, 12 mmol), the compound (3) {2-[2-(2-tert-butoxycarbonylaminoethoxy)ethoxy]ethyl bromide} (4.50 g, 14.4 mmol), anhydrous potassium carbonate (1.66 g, 12 mmol), $BU_4NI$ (554 mg, 1.5 mmol) and DMF (15 ml) was stirred at 60° C. for 14 hours in an atmosphere of argon gas. After that, the solvent of the reaction mixture was evaporated under reduced pressure, water was added to the resulting residue and the mixture was extracted with ethyl acetate. The extract was washed with water, 0.1N HCl and water successively and dried over anhydrous magnesium sulfate, the solvent was evaporated therefrom under reduced pressure and the residue was purified by a silica gel column chromatography (eluting with ethyl acetate:hexane=1:1) to give 5.33 g (96%) of the compound (4) {2-[2-[2-(2-tert-butoxycarbonylaminoethoxy)ethoxy]ethoxy]-4-[3-(trifluoromethyl)-3H-diazirine-3-yl]benzaldehyde as a pale yellow oily substance.

$^1$H NMR (400 MHz, CDCl$_3$, 25° C.): δ=10.5 (s, 1H), 7.85 (d, J=8.1 Hz, 1H), 6.86 (d, J=8.1 Hz, 1H), 6.75 (br s, 1H), 5.00 (br, 1H), 4.27 (t, J=4.8 Hz, 2H), 3.92 (t, J=4.8 Hz, 2H), 3.7 (m, 2H), 3.6 (m, 2H), 3.54 (t, J=5.1 Hz, 2H), 3.3 (m, 2H), 1.43 (s, 9H); MS (FAB$^+$): m/z (%): 484 (84) [M+Na]$^+$, 462 (4)

The compound (4) (3.69 g, 8 mmol) was dissolved in ethanol (40 ml) and NaBH$_4$ (303 mg, 8 mmol) was added to this solution gradually. After the reaction mixture was stirred at room temperature for 30 minutes, the solvent was evaporated therefrom under reduced pressure, water was added to the residue and the mixture was adjusted to pH around 3 by adding 1N HCl thereto at 0° C. and extracted with ethyl acetate. The extract was washed with water, saturated aqueous solution of sodium bicarbonate and saturated aqueous saline solution successively and dried over anhydrous magnesium sulfate and the solvent was evaporated therefrom under reduced pressure to give the crude compound (5) {2-[2-[2-(2-tert-butoxycarbonylaminoethoxy)ethoxy]ethoxy]-4-[3-(trifluoromethyl)-3H-diazirine-3-yl]benzylalchol as a pale yellow oily substance. This crude compound (5) was immediately used in the next step without further purification.

$^1$H NMR (400 MHz, CDCl$_3$, 25° C.): δ=7.26 (d, J=8.0 Hz, 1H), 6.79 (d, J=8.0 Hz, 1H), 6.66 (br s, 1H), 6.01 (br, 1H), 5.02 (br, 1H), 4.66 (s, 2H), 4.22 (t, J=4.8 Hz, 2H), 3.84 (t, J=4.8 Hz, 2H), 3.7 (m, 2H), 3.6 (m, 2H), 3.51 (t, J=5.1 Hz, 2H), 3.3 (m, 2H), 1.45 (s, 9H); MS (FAB$^+$): m/z (%): 486 (100) [M+Na]$^+$, 464 (16) (M+H)$^+$; HRMS: calc. for C$_{20}$H$_{29}$F$_3$N$_3$O$_6$ [M+H]$^+$=464.2008, found: 464.1997.

EXAMPLE 4

Manufacture of the Compound (6) from the Compound (5)

The crude compound (5) (3.69 g, 8 mmol) prepared from the compound (4) in the above step was dissolved in carbon tetrabromide (3.32 g, 10 mmol) and dichloromethane (16 ml) and then triphenyl phosphine (3.15 g, 12 mmol) was slowly added to the above mixture under cooling at 0° C. After ten minutes, anhydrous potassium carbonate (1.66 g, 12 mmol) was added to the reaction mixture followed by stirring at 0° C. for 30 minutes more. After that, water was added to the reaction mixture followed by extracting with dichloromethane, the extract was dried over anhydrous magnesium sulfate, the solvent was evaporated therefrom under reduced pressure and the residue was purified by a silica gel column chromatography (eluting with ethyl acetate:hexane=1:1) to give the compound (6) {2-[2-[2-(2-tert-butoxycarbonylaminoethoxy)ethoxy]ethoxy]-4-[3-(trifluoromethyl)-3H-diazirine-3-yl]benzylbromide (3.62 g, 86%) as a pale yellow oily substance.

$^1$H NMR (400 MHz, CDCl$_3$, 25° C.): δ=7.35 (d, J=8.1 Hz, 1H), 6.77 (d, J=8.1 Hz, 1H), 6.65 (br s, 1H), 5.00 (br, 1H), 4.51 (s, 2H), 4.21 (t, J=4.8 Hz, 2H), 3.91 (t, J=4.8 Hz, 2H), 3.75 (m, 2H), 3.65 (m, 2H), 3.55 (t, J=5.1 Hz, 2H), 3.3 (m, 2H), 1.43 (s, 9H); MS (FAB$^+$): m/z (%): 550 (41) [M+Na]$^+$, 548 (40), 528 (12) [M+H]$^+$, 526 (11); HRMS: calcd. for ($^{79}$Br) C$_{20}$H$_{28}$BrF$_3$N$_3$O$_5$ [M+H]$^+$=526.1164, found: 526.1193.

EXAMPLE 5

Manufacture of the Compound (7) from the Compound (6)

A mixture of the compound (6) (2.63 g, 5 mmol), N-hydroxyphthalimide (979 mg, 6 mmol), anhydrous potassium carbonate (691 mg, 5 mmol) and DMSO (10 ml) was stirred at room temperature for 12 hours. After that, the solvent of the reaction mixture was evaporated under reduced pressure using an oil pump, water was added to the residue and the mixture was extracted with ethyl acetate. The extract was washed with water, 1N NaOH and saturated aqueous saline solution successively and dried over anhydrous magnesium sulfate, the solvent was evaporated therefrom under reduced pressure and the residue was purified by a silica gel column chromatography (eluting with hexane:acetone=3:1) to give the compound (7) {2-[2-[2-(2-tert-butoxycarbonylaminoethoxy)ethoxy]ethoxy]-4-[3-(trifluoromethyl)-3H-diazirine-3-yl]benzyloxyphthalimide (2.59 g, 85%) as a pale yellow oily substance.

$^1$H NMR (400 MHz, CDCl$_3$, 25° C.): δ=7.82–7.73 (AB, 4H), 7.54 (d, J=7.9 Hz, 1H), 6.81 (d, J=7.9 Hz, 1H), 6.66 (br s, 1H), 5.27 (s, 2H), 5.05 (br, 1H), 4.15 (t, J=4.8 Hz, 2H), 3.86 (t, J=4.8 Hz, 2H), 3.7 (m, 2H), 3.6 (m, 2H), 3.54 (t, J=5.2 Hz, 2H), 3.3 (m, 2H), 1.42 (s, 9H), 1.42 (s, 9H); MS (FAB$^+$): m/z (%): 631 (100) [M+Na]$^+$, 609 (9) [M+H]$^+$; HRMS: calcd. for C$_{28}$H$_{32}$F$_3$N$_4$O$_8$ [M+H]$^+$=609.2172, found: 609.2164.

EXAMPLE 6

Manufacture of the Compound (8) from the Compound (7)

The compound (7) (304 mg, 0.5 mmol) was dissolved in dichloromethane (0.5 ml), trifluoroacetic acid (0.5 ml) was gradually added there under cooling at 0° C. and the reaction mixture was stirred at 0° C. for 1 hour. Toluene (1 ml) was added to the residue obtained by evaporation of the solvent under reduced pressure and the mixture was evaporated under reduced pressure. This operation was repeated for three times in total, a remaining excessive trifluoroacetic acid was removed, the resulting yellow oily residue was dissolved in DMF (0.5 ml), a solution of biotin N-hydroxysuccinimide ester (171 mg, 0.5 mmol) in DMF (2 ml) was added thereto and the reaction mixture was stirred at room temperature for 14 hours in the presence of a catalytic amount of triethylamine. After that, the solvent was evaporated therefrom under reduced pressure, the resulting residue was dissolved in a 1:1 mixture of dichloromethane and methanol, the solution was washed with 1N NaOH, saturated aqueous saline solution, 0.1N HCl and saturated aqueous saline solution successively and dried over anhydrous magnesium sulfate, the solvent was evaporated therefrom under reduced pressure and the residue was purified by a silica gel column chromatography (eluting with chloroform:ethanol=10:1) to give the compound (8) {2-[2-[2-(2-biotinylaminoethoxy)ethoxy]ethoxy]-4-[3-(trifluoromethyl)-3H-diazirine-3-yl]benzyloxyphthalimide (320 mg, 87%) as a colorless solid.

$^1$H NMR (400 MHz, CDCl$_3$, 25° C.): δ=7.83–7.73 (AB, 4H), 7.53 (d, J=7.9 Hz, 1H), 6.84 (s, 1H), 6.81 (d, J=7.9 Hz,

1H), 6.64 (s, 1H), 6.61 (s, 1H), 5.64 (s, 1H), 5.26 (s, 2H), 4.5 (m, 1H), 4.3 (m, 1H), 4.15 (t, J=4.8 Hz, 2H), 3.90 (t, J=4.8 Hz, 2H), 3.7 (m, 2H), 3.65 (m, 2H), 3.55 (m, 2H), 3.4 (br m, 2H), 3.1 (m, 1H), 2.9 (m, 1H), 2.72 (d, J=12.5 Hz, 1H). 2.19 (t, J=7.5 Hz, 2H), 1.8–1.6 (m, 4H), 1.4 (m, 2H); MS (FAB$^+$): m/z (%): 757 (16), [M+Na]$^+$, 735 (62) [M+H]$^+$; HRMS: calcd. for $C_{33}H_{38}F_3N_6O_8S$ [M+H]$^+$=735.2424, found: 735.2458.

EXAMPLE 7

Manufacture of the Compound (9) from the Compound (8)

The compound (8) (73 mg, 0.1 mmol) was dissolved in 1M methanol solution (1 ml) of anhydrous hydrazine and the reaction was carried out at room temperature for 30 minutes. After that, the solvent was evaporated therefrom under reduced pressure and toluene (1 ml) was added to the resulting residue followed by evaporating under reduced pressure. This operation was repeated for three times and the remaining excessive hydrazine was removed to give a crude compound (9) as a colorless solid. This was immediately used in the next reaction without further purification.

EXAMPLE 8

Manufacture of the Compound (10) from the Compound (9)

The crude compound (9) prepared from the compound (8) (73 mg, 0.1 mmol) in the above step was dissolved in a 1:1 mixture (1 ml) of chloroform and acetonitrile and made to react with [(CH$_3$)$_3$COCO]$_2$O (109 mg, 0.5 mmol) in the presence of triethylamine (51 mg, 0.5 mmol) at room temperature for 14 hours. After that, the solvent was evaporated therefrom under reduced pressure and the residue was purified by a silica gel column chromatography (eluting with chloroform:ethanol=10:1) to give a compound (10) {2-[2-[2-(2-biotinylaminoethoxy)ethoxy]ethoxy]-4-[3-(trifluoromethyl)-3H-diazirine-3-yl]benzyloxycarbamic tert-butylester (64 mg, 95%) as a colorless solid.

$^1$H NMR (400 MHz, CDCl$_3$, 25° C.): δ=8.31 (s, 1H), 7.39 (d, J=7.9 Hz, 1H), 6.97 (br, 1H), 6.81 (d, J=7.9 Hz, 1H), 6.64 (s, 1H), 6.58 (s, 1H), 5.66 (s, 1H), 4.91 (s, 2H), 4.5 (m, 1H), 4.3 (m, 1H), 4.16 (t, J=4.5 Hz, 2H), 3.87 (t, J=4.5 Hz, 2H), 3.7 (m, 2H), 3.65 (m, 2H), 3.55 (m, 2H), 3.4 (br m, 2H), 3.1 (m, 1H), 2.9 (m, 1H), 2.70 (d, J=12.8 Hz, 1H), 2.17 (t, J=7.3 Hz, 2H), 1.8–1.6 (m, 4H), 1.45 (s, 9H), 1.4 (m, 2H); UV/VIS (MeOH): λ$_{max}$ (ε)=360 (400), 283 (2600); MS (FAB$^+$): m/z (%): 727 (100), [M+Na]$^+$, 705 (12) [M+H]$^+$; HRMS: calcd. for $C_{30}H_{44}F_3N_6O_8S$ [M+H]$^+$=705.2893, found: 705.2853.

EXAMPLE 9

Manufacture of the Compound (11) from the Compound (10)

The compound (10) (7 mg, 0.01 mmol) was dissolved in dichloromethane (0.1 ml), then trifluoroacetic acid (0.1 ml) was gradually added thereto while cooling at 0° C. and the reaction was carried out at 0° C. for 1 hour. After that, the solvent was evaporated therefrom under reduced pressure and toluene (0.1 ml) was added to the residue followed by evaporating under reduced pressure. This operation was repeated for three times to remove the remaining excessive trifluoroacetic acid whereupon the compound (11), a pale yellow solid, was prepared. This was immediately used in a condensation reaction with a saccharide compound without further purification.

EXAMPLE 10

Manufacture of the Compound (12) from the Compound (11)

The crude compound (11) prepared from the compound (10) (7 mg, 0.01 mmol) was dissolved in acetonitrile (0.1 ml), an aqueous solution of N-acetyllactosamine (1.9 mg, 0.005 mmol) was added thereto and the reaction was carried out at −37° C. for 40 hours. The reaction mixture was purified by means of an HPLC using a silica gel column (Aquasil SS-1251-120, 4.6f×250 mm, manufactured by Senshu Kagaku). The yield was calculated by measuring the UV spectrum of a methanolic solution using an UV spectrum of the compound (11) (361 nm (e=386)) as a standard whereupon the compound (12) was found to be prepared in 0.0031 mmol (63%). Conditions for the HPLC: 90% aq. CH$_3$CN→75% aq. CH$_3$CN, 20 min, 1 ml/min. Negative ion FAB-MS (3-nitrobenzyl alcohol) m/z: 968 [M−H]$^-$ HR-FAB-MS (3-nitrobenzyl alcohol). Calcd. for $C_{39}H_{57}F_3N_7O_{16}S$ ([M−H]$^-$): 968.3535; found 968.3586.

EXAMPLE 11

Manufacture of the Compound (13) from the Compound (11)

The compound (11) prepared from the compound (10) (3.5 mg, 0.005 mmol) in Example 9 was made to react with sialyl-α2-3-lactose (1.6 mg, 0.0025 mmol) under the same condition as in Example 10 and similarly purified by means of an HPLC to give the compound (13) (0.0012 mmol, 48%). Conditions for the HPLC: 95% aq. CH$_3$CN→50% aq. CH$_3$CN, 10 min, 1 ml/min. Negative ion FAB-MS (3-nitrobenzyl alcohol) m/z: 1218 [M−H]$^-$ HR-FAB-MS (3-nitrobenzyl alcohol). Calcd. for $C_{48}H_{71}F_3N_7O_{24}S$ ([M−H]$^-$): 1218.4223; found 1218.4257.

EXAMPLE 12

Manufacture of the Compound (14) from the Compound (11)

The compound (11) prepared from the compound (10) (4.3 mg, 0.006 mmol) by the method of Example 9 was made to react with sialyl-α2-3-N-acetyllactosamine (95% purity, 1.0 mg, 0.0014 mmol) under the same condition as in Example 10 and similarly purified by means of an HPLC to give the compound (14) (0.00085 mmol, 61%). Conditions for the HPLC: 85% aq. CH$_3$CN→70% aq. CH$_3$CN, 15 min, 1 ml/min. Negative ion FAB-MS (3-nitrobenzyl alcohol) m/z: 1259 [M−H]$^-$ HR-FAB-MS (3-nitrobenzyl alcohol). Calcd. for $C_{50}H_{74}F_3N_8O_{24}S$ ([M−H]$^-$): 1259.4489; found 1259.4507.

EXAMPLE 13

Manufacture of the Compound (15) from the Compound (11)

The compound (11) prepared from the compound (10) (1.4 mg, 0.002 mmol) by the method of Example 9 was made to react with Lewis X type trisaccharide (0.5 mg, 0.00094 mmol) under the same condition as in Example 10 and similarly purified by means of an HPLC to give the compound (15) (0.00073 mmol, 78%). Conditions for the HPLC: 90% aq. CH$_3$CN→70% aq. CH$_3$CN, 15 min, 1 ml/min. Negative ion FAB-MS (3-nitrobenzyl alcohol) m/z: 1114 [M−H]$^-$ HR-FAB-MS (3-nitrobenzyl alcohol). Calcd. for $C_{45}H_{66}F_3N_7O_{20}S$ ([M−H]$^-$): 1114.4114; found 1114.4163.

EXAMPLE 14

Manufacture of the Compound (16) from the Compound (11)

The compound (11) prepared from the compound (10) (1.7 mg, 0.0024 mmol) by the method of Example 9 was made to react with sialyl Lewis X type tetrasaccharide (95% purity; 1 mg, 0.0012 mmol) under the same condition as in Example 10 and similarly purified by means of an HPLC to give the compound (16) (0.00085 mmol, 71%). Conditions for the HPLC: 85% aq. $CH_3CN \rightarrow 65\%$ aq. $CH_3CN$, 15 min, 1 ml/min. Negative ion FAB-MS (3-nitrobenzyl alcohol) m/z: 1405 [M–H]$^-$ HR-FAB-MS (3-nitrobenzyl alcohol). Calcd. for $C_{56}H_{84}F_3N_8O_{28}S$ ([M–H]$^-$): 1405.5068; found 1405.5143.

EXAMPLE 15

Manufacture of the Compound (17)

Sodium hydride (8.0 g, 60% oily dispersion, 0.2 mol) was suspended in toluene (200 ml) and 2-[2-(2-chloroethoxy)ethoxy]ethanol (33.7 g, 0.2 mol) was gradually added thereto at −70° C. Ethyl bromoacetate (33.4 g, 0.2 mol) was gradually dropped into the above mixture at −70° C. and, after 30 minutes, the reaction mixture was allowed to stand at room temperature. After 2 hours, acetic acid was added to the reaction mixture at 0° C. to neutralize, then the solvent was evaporated therefrom under reduced pressure and the residue was purified by a silica gel column chromatography (eluting with ethyl acetate:hexane=3:2) to give a colorless oily substance (38.8 g). This was dissolved in N-methyl-1-2-pyrrolidone (200 ml), then ethyl bromide (163 g, 1.5 mol) and sodium bromide (3.1 g, 0.03 mol) were added thereto and the mixture was heated at 65° C. for 48 hours. The solvent was evaporated therefrom under reduced pressure and the residue was purified by a silica gel column chromatography (eluting with ethyl acetate:hexane=3:2) to give the compound (17) {2-[2-(2-bromoethoxy)ethoxy]ethoxy ethyl acetate} (32.3 g, 76%) as a colorless oily substance.

$^1$H NMR (400 MHz, CDCl$_3$, 25° C.): δ=1.28 (3H, t, J=7.3 Hz, —CH$_2$—CH$_3$), 3.47 (2H, t, J=6.3 Hz, BrCH$_2$), 3.68–3.75 (8H, m, O—CH$_2$—), 3.81 (2H, t, J=6.3 Hz, Br CH$_2$CH$_2$O), 4.15 (2H, s, O—CH$_2$—CO—), 4.23 (2H, q, J=7.3 Hz, —CH$_2$—CH$_3$).

EXAMPLE 16

Manufacture of the Compound (18) from the Compounds (2) and (17)

A mixture of the compound (2) (4.62 g, 20 mmol), the compound (17) (7.18 g, 24 mmol), anhydrous potassium carbonate (2.76 g, 20 mmol), Bu$_4$NI (7.39 g, 20 mmol) and DMSO (20 ml) was stirred in an argon gas atmosphere at 60° C. for 14 hours. After that, water was added to the reaction solution and the mixture was extracted with ethyl acetate. The extract was washed with water, 0.1N HCl and water successively and dried over anhydrous magnesium sulfate, the solvent was evaporated therefrom under reduced pressure and the residue was purified by a silica gel column chromatography (eluting with diethyl ether:hexane=3:1) to give the compound (18) {2-[2-[2-(2-ethoxycarbonylmethoxy)ethoxy)ethoxy]ethoxy]-4-[3-(trifluoromethyl)-3H-diazirine-3-yl]benzaldehyde (6.58 g, 76%) as a pale yellow oily substance.

$^1$H NMR (400 MHz, CDCl$_3$, 25° C.): δ=1.28 (3H, t, J=7.3 Hz, —CH$_2$—CH$_3$), 3.67–3.93 (12H, m, O—CH$_2$—), 4.14 (2H, s, O—CH$_2$—CO—), 4.20 (2H, q, J=7.3 Hz, —CH$_2$—CH$_3$), 4.52 (2H,s, Ph—CH$_2$—), 6.74 (1H, s, Ph—H), 6.85 (1H, d, J=8.1 Hz, Ph—H), 7.84 (1H, d, J=8.1 Hz, Ph—H). UV (EtOH) nm (ε): 210 (16,368), 289.5 (1,272).

EXAMPLE 17

Manufacture of the Compound (19) from the Compound (18)

The compound (18) (2.17 g, 5 mmol) was dissolved in ethanol (10 ml) and NaBH$_4$ (189 g, 5 mmol) was gradually added to the resulting solution. After the reaction mixture was stirred at room temperature for 30 minutes, acetic acid was added to the reaction solution at 0° C. to adjust the pH to around 3, the solvent was evaporated therefrom under reduced pressure and the residue was extracted with ethyl acetate The extract was washed with 0.1N HCl, water and a saturated aqueous saline solution successively and dried over anhydrous magnesium sulfate, the solvent was evaporated therefrom under reduced pressure and the residue was purified by a silica gel column chromatography (eluting with ethyl acetate:hexane=1:1) to give the compound (19) {2-[2-[2-(2-ethoxycarbonylmethoxy)ethoxy)ethoxy]ethoxy]-4-[3-(trifluoromethyl)-3H-diazirine-3-yl]benzylalchol (1.72 g, 76%) as a pale yellow oily substance.

$^1$H NMR (400 MHz, CDCl$_3$, 25° C.): δ=1.28 (3H, t, J=7.3 Hz, —CH$_2$—CH$_3$), 3.43–3.87 (12H, m, O—CH$_2$—), 4.12 (2H, s, O—CH$_2$—CO—), 4.20 (2H, q, J=7.3 Hz, —CH$_2$—CH$_3$), 4.52 (2H, s, Ph—CH$_2$—), 6.62 (1H, s, Ph—H), 6.79 (1H, d, J=7.8 Hz, Ph—H), 7.30 (1H, d, J=7.8 Hz, Ph—H); UV (EtOH) nm (ε): 206.5 (24,660), 227 (10,244), 280 (2,311).

EXAMPLE 18

Manufacture of the Compound (20) from the Compound (19)

The compound (19) (3.60 g, 8 mmol) and carbon tetrabromide (3.32 g, 10 mmol) were dissolved in dichloromethane (16 ml) and then triphenylphosphine (3.15 g, 12 mmol) was gradually added thereto under cooling at 0° C. After 30 minutes, water was added to the reaction mixture, the mixture was extracted with dichloromethane, the extract was dried over anhydrous magnesium sulfate, the solvent was evaporated therefrom under reduced pressure and the residue was purified by a silica gel column chromatography (eluting with ethyl acetate:hexane=1:1) to give the compound (20) {2-[2-[2-(2-ethoxycarbonylmethoxy)ethoxy)ethoxy]ethoxy]-4-[3-(trifluoromethyl)-3H-diazirine-3-yl]benzylbromide (3.37 g, 82%) as a pale yellow oily substance.

$^1$H NMR (400 MHz, CDCl$_3$, 25° C.): δ=1.28 (3H, t, J=7.3 Hz, —CH$_2$—CH$_3$), 3.67–3.91 (12H, m, O—CH$_2$—), 4.14 (2H, s, O—CH$_2$—CO—), 4.20 (2H, q, J=7.3 Hz, —CH$_2$—CH$_3$), 4.52 (2H, s, Ph—CH$_2$—), 6.65 (1H, s, Ph—H), 6.77 (1H, d, J=8.0 Hz, Ph—H), 7.35 (1H, d, J=8.0 Hz, Ph—H). Positive ion FABMS (3-nitrobenzylalcohol) m/z: 535 (M+H)$^+$. UV (EtOH) nm (ε): 209 (23,783), 238.5 (8,873), 290 (2,927).

EXAMPLE 19

Manufacture of the Compound (22) from the Compounds (20) and (21)

Sodium hydride (216 mg, 60% oily dispersion, 5.4 mmol) was suspended in THF (10 ml) and tert-butyl N-hydroxycarbamate (the compound (21)) (718 mg, 6 mmol) was added thereto under cooling at −20° C. After 15 minutes, the compound (20) (2.31 g, 4.5 mmol) was added thereto under cooling at −15° C. and the reaction mixture was stirred at 0° C. After 2 hours, the reaction solution was adjusted to pH around 3 by adding 1N HCl thereto at 0° C. and extracted with ethyl acetate. The extract was dried over anhydrous magnesium sulfate, the solvent was evaporated therefrom under reduced pressure and the residue was purified by a silica gel column chromatography (eluting with hexane:diethyl ether=1:10) to give the compound (22) {2-[2-[2-(2-ethoxycarbonylmethoxy)ethoxy)ethoxy]ethoxy]-4-[3-(trifluoromethyl)-3H-diazirine-3-yl]benzyloxycarbamic tert-butylester (2.11 g, 83%) as a pale yellow oily substance.

$^1$H NMR (400 MHz, CDCl$_3$, 25° C.): δ=1.28 (3H, t, J=7.1 Hz, —CH$_2$—CH$_3$), 1.46 (9H, s, —C(CH$_3$)$_3$), 3.67–3.88 (12H, m, O—CH$_2$—), 4.12 (2H, s, O—CH$_2$—CO—), 4.20 (2H, q, J=7.1 Hz, —CH$_2$—CH$_3$), 4.91 (2H, s, Ph—CH$_2$—), 6.65 (1H, s, Ph—H), 6.79 (1H, d, J=8.0 Hz, Ph—H), 7.38 (1H, d, J=8.0 Hz, Ph—H), 7.67 (1H, s, NH). FABMS (3-nitrobenzylalcohol) m/z, 588 (M+H)$^+$. UV: 207 nm (ε34029), 228.5 nm (ε13228), 280.5 nm (ε2959).

EXAMPLE 20

Manufacture of the Compound (23) from the Compound (22)

The compound (22) (2.26 g, 4 mmol) was dissolved in a mixed solvent of 1N NaOH (20 ml) and ethanol (18 ml) and the solution was stirred at 0° C. for 30 minutes. The reaction solution was adjusted to pH around 3 by adding 1N HCl thereto at 0° C., the solvent was evaporated therefrom under reduced pressure and the residue was purified by a silica gel column chromatography (eluting with chloroform:methanol=5:1) to give the compound (23) {2-[2-[2-(2-carboxymethoxy)ethoxy]ethoxyethoxy]-4-[3-(trifluoromethyl)-3H-diazirine-3-yl]benzyloxycarbamic tert-butylester (2.1 g, 98%) as a pale yellow oily substance.

$^1$H NMR (400 MHz, CDCl$_3$, 25° C.): δ=1.46 (9H, s, —C(CH$_3$)$_3$), 3.69–3.90 (12H, m, O—CH$_2$—), 4.13 (2H, bs, O—CH$_2$—CO—), 4.91 (2H, s, Ph—CH$_2$—), 6.65 (1H, s, Ph—H), 6.81 (1H, d, J=7.8 Hz, Ph—H), 7.37 (1H, d, J=7.8 Hz, Ph—H), 8.06 (1H, bs, NH).

EXAMPLE 21

Manufacture of the Compound (25) from the Compounds (23) and (24)

The compound (23) (537 mg, 1 mmol) and carbonyl diimidazole (194 mg, 1.2 mmol) were dissolved in anhydrous THF (1 ml), then methyl sulfamoylbenzoate (the compound (24)) (258 mg, 1.2 mmol) and diisopropyl ethylamine (158 mg, 1.2 mmol) were added thereto as stirring at room temperature and the mixture was made to react at room temperature for 18 hours. After that, the solvent was evaporated therefrom under reduced pressure, water was added to the residue and the mixture was extracted with ethyl acetate. The extract was washed with 0.5N HCl, a saturated aqueous solution of sodium bicarbonate and a saturated aqueous saline solution successively, dried over anhydrous magnesium sulfate, the solvent was evaporated therefrom under reduced pressure and the residue was purified by a silica gel column chromatography (eluting with ethyl acetate:ethanol=10:1) to give the compound (25) (734 mg, 74%) as a pale yellow oily substance.

$^1$H NMR (400 MHz, CDCl$_3$, 25° C.): δ=1.40 (9H, s, —C(CH$_3$)$_3$), 3.69–3.90 (12H, m, O—CH$_2$—), 3.94 (3H, s, CH$_3$), 4.2 (2H, bs, O—CH$_2$—CO—), 5.02 (2H, s, Ph—CH$_2$—), 6.67 (1H, s, Ph—H), 6.80 (1H, d, J=7.8 Hz, Ph—H), 7.34 (1H, d, J=7.8 Hz, Ph—H), 7.69 (1H, s, NH), 8.14 (4H, s, Ph—H).

EXAMPLE 22

Manufacture of the Compound (26) from the Compound (25)

The compound (25) (120 mg, 0.15 mmol) was dissolved in a mixed solvent of 1N NaOH (0.75 ml) and ethanol (3.5 ml) and the solution was stirred at 0° C. for 30 minutes. This was adjusted to pH around 3 by adding 5N HCl (0.15 ml) under cooling at 0° C. and extracted with ethyl acetate. The extract was washed with a saturated aqueous saline solution and dried over anhydrous magnesium sulfate, the solvent was evaporated therefrom under reduced pressure and the residue was purified by a silica gel column chromatography (eluting with chloroform:methanol=5:1) to give the compound (26) (99 mg, 89%) as a pale yellow oily substance.

$^1$H NMR (400 MHz, CDCl$_3$, 25° C.): δ=1.43 (9H, s, —C(CH$_3$)$_3$), 3.68–4.10 (12H, m, O—CH$_2$—), 4.23 (2H, s, O—CH$_2$—CO—), 4.91 (2H, s, Ph—CH$_2$—), 6.65 (1H, s, Ph—H), 6.77 (1H, d, J=8.1 Hz, Ph—H), Ph—H 7.35 (1H, d, J=8.1 Hz, Ph—H), 8.17–8.23 (4H, m, Ph—H), 8.03 (1H, bs, —NH).

EXAMPLE 23

Manufacture of the Compound (28) from the Compounds (26) and (27)

The compound (26) (72 mg, 0.1 mmol) was dissolved in 1 ml of dichloromethane, then N-hydroxysuccinimide (13 mg, 0.11 mmol) and DCC (23 mg, 0.11 mmol) were added thereto and the mixture was stirred at room temperature for 1 hour. The solvent was evaporated therefrom under reduced pressure, the residue was dissolved in DMSO (1 ml), biotin hydrazide (compound (27)) (26 mg, 0.1 mmol) was added thereto and the mixture was stirred overnight at room temperature. The reaction solution was directly purified by a silica gel column chromatography (eluting with chloroform:methanol=5:1) to give the compound (28) (10 mg, 10%) as a pale yellow solid. Positive ion FABMS (3-nitrobenzylalcohol) m/z: 961 (M+H)$^+$.

EXAMPLE 24

Manufacture of the Compound (29) from the Compound (11)

The compound (11) prepared from the compound (10) (3.5 mg, 5 μmol) by the method of Example 9 was made to react with chitobiose (1.1 mg, 2.5 μmol) under the same condition as Example 10. Then the same purification by an HPLC was carried out to give the compound (29) (1.2 μmol, 48%). The conditions for the HPLC: 85% aq. CH$_3$CN, 1 ml/min. Positive ion FAB-MS (3-nitrobenzylalcohol) m/z: 1011 (M+H)$^+$, 1033 (M+Na)$^+$.

EXAMPLE 25

Manufacture of the Compound (30) from the Compound (28)

The compound (28) (9.6 mg, 10 μmol) was deprotected by the method of Example 9 and then made to react with chitobiose (2.1 mg, 5 μmol) under the same condition as in Example 10. Then the same purification by an HPLC was carried out to give the compound (30) (0.1 μmol, 2%). Conditions for the HPLC: 90% aq. CH₃CN→80% aq. CH₃CN, 20 min, 1 ml/min. Positive ion FAB-MS (3-nitrobenzylalcohol) m/z: 1266 (M+H)⁺, 1288 (M+Na)⁺.

REFERENTIAL EXAMPLE 1

Photoaffinity Labeling Experiment for Lectin

A photoaffinity labeling experiment for the compounds (12)–(16) was carried out as follows according to a method of Hatanaka, et al. (Y. Hatanaka, M. Hashimoto, H. Nishihara, H. Narimatsu, Y. Kanaoka: Carbohydr. Res., vol. 294, pages 95–108 (1996)).

Thus, 0.05 ml each of photoaffinity labeling sample containing photoaffinity labeling reagent (0.1 mM) selected from any of the compounds (12)–(16) and lectin (subunit concentration: 0.1 mM) in 0.1M phosphate buffer (pH 7.6) was prepared. In the meanwhile, 0.05 ml each of control sample containing photoaffinity labeling reagent (0.1 mM) selected from any of the compounds (12)–(16), lectin (0.1 mM per subunit) and an inhibitor (0.1M) in 0.1M phosphate buffer (pH 7.6) was prepared. Combinations of the photoaffinity labeling reagent, lectin and the inhibitor (in the case of the control test) in this order are as follows.

Compound (12), Lectin from *Ricinus communis* (RCA) and N-Acetyllactosamine;

Compound (13), Lectin from wheat germ agglutinin (WGA) and Sialyl-α2-3-lactose;

Compound (14), Lectin from *Maackia amurensis* (MAL) and Sialyl-α2-3-lactose;

Compound (15), Lectin from lotus (Lotus) and Methyl-α-fucopyranoside; and

Compound (16), Lectin from *Maackia amurensis* (MAL) and Sialyl-α2-3-lactose.

The photoaffinity labeling reagent samples and control samples prepared as above were incubated in the darkness at 25° C. for 30 minutes and then irradiated with a 30-watt long-wavelength UV lamp (Funakoshi XX-15) for one hour at the distance of 5 cm from above at 0° C. on ice. Each of the samples after irradiation was separated by a conventional method by means of a 12% SDS-polyacrylamide electrophoresis, transcribed to a PVDF membrane and a photolabeling band was detected by means of a chemiluminescence analysis. Since the photolabeling was inhibited in the control test, it was confirmed that the label was specific to each lectin. The result is shown in Table 1.

TABLE 1

| Labeling Reagent | Lectin | MW of Photolabeling Band |
| --- | --- | --- |
| Compound (12) | RCA | 35,000 |
| Compound (13) | WGA | 22,000 |
| Compound (14) | MAL | 35,000 |
| Compound (15) | Lotus | 28,000 |
| Compound (16) | MAL | 35,000 |

REFERENTIAL EXAMPLE 2

Photoaffinity Labeling Experiment for WGA

The photoaffinity labeling experiment of the compounds (29) and (30) was carried out by the same method as in Referential Example 1.

Thus, 0.05 ml each of photoaffinity labeling sample containing photoaffinity labeling reagent (0.1 mM) selected from either of the compounds (29) and (30) and WGA (subunit concentration: 0.1 mM) in 0.1M phosphate buffer (pH 7.6) was prepared. In the meanwhile, 0.05 ml each of control sample containing photoaffinity labeling reagent (0.1 mM) selected from either of the compounds (29) and (30), WGA (subunit concentration: 0.1 mM) and chitobiose (0.1M) in 0.1M phosphate buffer (pH 7.6) was prepared.

The photoaffinity labeling samples and control samples prepared as above were incubated in the darkness at 25° C. for 30 minutes and then irradiated with a 30-watt long-wavelength UV lamp (Funakoshi XX-15) for one hour at the distance of 5 cm from above at 0° C. on ice. Each of the samples after irradiation was separated by a conventional method by means of a 12% SDS-polyacrylamide electrophoresis, transcribed to a PVDF membrane and a photolabeling band was detected by means of a chemiluminescence analysis. Since the photolabeling of the band of WGA of molecular weight of 22 k was inhibited in the control test, it was confirmed that the label was specific to WGA.

Cleavage of the spacer was carried out as follows. Each sample (10 μl) after irradiation was dissolved in 0.5M Tris hydrochloride buffer (pH 8.5, 10 μl) containing 7M guanidine and EDTA 2Na (10 mM), then 0.7M DTT (10 μl) was added and the mixture was made to react at room temperature for 2 hours. The reactions were further carried out with 1M sodium iodoacetate (10 μl) at room temperature for 4 hours and then with 4M mercaptoethanol for 5 hours more, the reaction mixture was dialyzed against 0.1M phosphate buffer (pH 7.6) and the analysis was similarly carried out by means of electrophoresis. After the cleavage reaction, molecular weight 22 k of WGA label band by the compound (30) disappeared and, therefore, the cleavage was confirmed.

The compounds of the present invention represented by the formula (II), particularly the above-mentioned compound (11) having an oxyamino group and salt thereof, are able to introduce saccharide-linked phenyldiazirine compounds of the formula (V) having a photoreactive group (diazirine) and biotin by a one-step synthesis without any particular protecting treatment and the compounds of the formula (V) are very useful as photoaffinity labeling reagents for a biotin-labeling of proteins (saccharide receptors) interacting with saccharide. Further, the compounds of the formula (V) where biotin is bound to a phenyldiazirine skeleton via a cleavable spacer are excellent in isolation and recovery of the labeled protein. Accordingly, the compounds of the formula (II) are stable and useful compounds for the easy manufacture of photoaffinity labeling reagents and the compounds of the formula (I) are highly useful compounds as intermediates for the synthesis of the compounds of the formula (II).

What is claimed is:

1. A phenyldiazirine compound of the following formula (I)

wherein R¹ is —NHP¹ or —COX¹; R² is an aldehyde group, a hydroxy lower alkyl group, a halogenated lower alkyl group, a phthalimidoxy lower alkyl group or —(CH$_2$)$_x$—O—NHP$^1$; P$^1$ is a protective group for an amino group; X$^1$ is an alkoxy group, a hydroxyl group or —NHSO$_2$—X$^2$—CO—X$^3$; X$^2$ is an arylene group or an alkylene group; X$^3$ is an alkoxy group or a hydroxyl group; m is an integer of from 1 to 4; n is an integer of from 1 to 6; and x is an integer of from 1 to 4.

2. A biotinylated phenyldiazirine compound of the following formula (II)

(II)

wherein R$^3$ is a phthalimide group, an amino group, —NHP$^1$ or salt of an amino group; P$^1$ is a protective group for an amino group; Y$^1$ is —NH— or —CONHSO$_2$—X$^2$—CO—; X$^2$ is an arylene group or an alkylene group; Y$^2$ is a biotin residue or a biotin derivative residue; m is an integer of from 1 to 4; n is an integer of from 1 to 6; and x is an integer of from 1 to 4.

3. A biotinylated phenyldiazirine compound claimed in claim 2, represented by the following formula (III)

(III)

wherein R$^3$ is a phthalimide group, an amino group, —NHP$^1$ or salt of an amino group; P$^1$ is a protective group for an amino group; m is an integer of from 1 to 4; n is an integer of from 1 to 6; and x is an integer of from 1 to 4.

4. A biotinylated phenyldiazirine compound claimed in claim 2, represented by the following formula (IV)

(IV)

wherein R$^3$ is a phthalimide group, an amino group, —NHP$^1$ or salt of an amino group; P$^1$ is a protective group for an amino group; m is an integer of from 1 to 4; n is an integer of from 1 to 6; X$^2$ is an arylene group or an alkylene group; Z is an alkylene group having 1 to 20 carbon atoms which may be interrupted by a hetero atom; x is an integer of from 1 to 4; and q is an integer of 0 or 1.

5. A saccharide-linked biotinylated phenyldiazirine compound of the following formula (V)

(V)

wherein R$^4$ is a residual group of a saccharide compound having a reducing end; Y$^1$ is —NH— or —CONHSO$_2$—X$^2$—CO—; X$^2$ is an arylene group or an alkylene group; Y$^2$ is a biotin residue or a biotin derivative residue; m is an integer of from 1 to 4; n is an integer of from 1 to 6; and x is an integer of from 1 to 4.

6. A saccharide-linked biotinylated phenyldiazirine compound of the following formula (VI)

(VI)

wherein $R^4$ is a residual group of a saccharide compound having a reducing end; m is an integer of from 1 to 4; n is an integer of from 1 to 6; and x is an integer of from 1 to 4.

7. A saccharide-linked biotinylated phenyldiazirine compound of the following formula (VII)

(VII)

wherein $R^4$ is a residual group of a saccharide compound having a reducing end; $X^2$ is an arylene group or an alkylene group; Z is an alkylene group having 1 to 20 carbon atoms which may be interrupted by a hetero atom; m is an integer of from 1 to 4; n is an integer of from 1 to 6; x is an integer of from 1 to 4; and q is an integer of 0 or 1.

8. A photoreactive labeling reagent containing the biotinylated phenyldiazirine compound of the formula (II) as mentioned in claim 2 where, in the formula (II), $R^3$ is an amino group or salt of an amino group.

9. A photoreactive labeling reagent containing the biotinylated phenyldiazirine compound of the formula (III) as mentioned in claim 3 where, in the formula (III), $R^3$ is an amino group or salt of an amino group.

10. A photoreactive labeling reagent containing the biotinylated phenyldiazirine compound of the formula (IV) as mentioned in claim 4 where, in the formula (IV), $R^3$ is an amino group or salt of an amino group.

11. A photoaffinity labeling reagent containing the saccharide-linked biotinylated phenyldiazirine compound of the formula (V) as mentioned in claim 5.

12. A photoaffinity labeling reagent containing the saccharide-linked biotinylated phenyldiazirine compound of the formula (VI) as mentioned in claim 6.

13. A photoaffinity labeling reagent containing the saccharide-linked biotinylated phenyldiazirine compound of the formula (VII) as mentioned in claim 7.

14. A method for the manufacture of the saccharide-linked biotinylated phenyldiazirine compound of the formula (V), which comprises reacting the biotinylated phenyldiazirine compound of the formula (II) with a saccharide compound having a reducing end to form a Schiff's base between an aldehyde group of the reducing end of the saccharide compound and an amino group of the biotinylated phenyldiazirine compound where $R^3$ in the formula (II) is an amino group or salt of an amino group.

15. The method claimed in claim 14, wherein the biotinylated phenyldiazirine compound is represented by the formula (III) and the saccharide-linked biotinylated phenyldiazirine compound is represented by the formula (VI).

16. The method claimed in claim 14, wherein the biotinylated phenyldiazirine compound is represented by the formula (IV) and the saccharide-linked biotinylated phenyldiazirine compound is represented by the formula (VII).

17. A method for labeling a saccharide receptor which comprises mixing the saccharide-linked biotinylated phenyldiazirine compound of the formula (V) with a saccharide receptor to bind them by a specific interaction between the residual group of the saccharide compound of the phenyldiazirine compound and the saccharide receptor, irradiating light to the mixture to bind the compound of the formula (V) by means of a photoreaction to a moiety of the saccharide receptor which interacts with the saccharide moiety of the compound represented by the formula (V) and thereby labeling the saccharide receptor.

18. The method for labeling the saccharide receptor, claimed in claim 17, wherein the saccharide-linked biotinylated phenyldiazirine compound is represented by the formula (VI).

19. The method for labeling the saccharide receptor, claimed in claim 17, wherein the saccharide-linked biotinylated phenyldiazirine compound is represented by the formula (VII).

* * * * *